(12) United States Patent
Triplett et al.

(10) Patent No.: US 11,806,005 B2
(45) Date of Patent: Nov. 7, 2023

(54) DEVICES AND METHODS FOR ANCHORING TISSUE

(71) Applicant: Crossroads Extremity Systems, LLC, Memphis, TN (US)

(72) Inventors: Daniel J. Triplett, Providence, UT (US); T. Wade Fallin, Hyde Park, UT (US)

(73) Assignee: Crossroads Extremity Systems, LLC, Memphis, TN (US)

( * ) Notice: Subject to any disclaimer, the term of this patent is extended or adjusted under 35 U.S.C. 154(b) by 468 days.

(21) Appl. No.: 16/871,454

(22) Filed: May 11, 2020

(65) Prior Publication Data

US 2020/0281581 A1 Sep. 10, 2020

Related U.S. Application Data

(63) Continuation of application No. 15/357,197, filed on Nov. 21, 2016, now Pat. No. 10,653,409.

(60) Provisional application No. 62/263,250, filed on Dec. 4, 2015.

(51) Int. Cl.
| | | |
|---|---|---|
| *A61B 17/04* | (2006.01) | |
| *A61F 2/08* | (2006.01) | |
| *A61B 17/16* | (2006.01) | |
| *A61B 17/06* | (2006.01) | |

(Continued)

(52) U.S. Cl.
CPC ...... *A61B 17/0401* (2013.01); *A61B 17/1682* (2013.01); *A61F 2/0805* (2013.01); *A61F 2/0811* (2013.01); *A61B 17/06128* (2013.01); *A61B 2017/00367* (2013.01); *A61B 2017/0404* (2013.01); *A61B 2017/0409* (2013.01); *A61B 2017/0417* (2013.01); *A61B 2090/034* (2016.02); *A61B 2090/062* (2016.02);
(Continued)

(58) Field of Classification Search
CPC ............ A61B 17/0401; A61B 17/0469; A61B 2017/04003; A61B 2017/0404; A61B 2017/0409; A61B 2017/0417; A61B 2017/00367; A61B 2017/00389; A61B 2090/062; A61F 2/0811
See application file for complete search history.

(56) References Cited

U.S. PATENT DOCUMENTS

| | | |
|---|---|---|
| 2,485,531 A | 10/1949 | William et al. |
| 3,620,216 A | 11/1971 | Szymanski |
| 3,664,345 A | 5/1972 | Dabbs et al. |

(Continued)

FOREIGN PATENT DOCUMENTS

| | | |
|---|---|---|
| KR | 10-2015-0107824 A | 9/2015 |
| WO | 97/20522 A1 | 6/1997 |

(Continued)

OTHER PUBLICATIONS

Arthrex Hallux Valgus Solutions, Arthrex, Inc., www.arthrex.com 2009, 2 pp.

(Continued)

*Primary Examiner* — Robert A Lynch
(74) *Attorney, Agent, or Firm* — BakerHostetler

(57) ABSTRACT

Devices and methods for anchoring soft tissue, tissue grafts, and the like to a bone are provided. In one example, an assembly includes a suture anchor, suture, and inserter. In another example, a method provides for reattaching soft tissue to a bone.

16 Claims, 13 Drawing Sheets

(51) Int. Cl.
  *A61B 90/00*  (2016.01)
  *A61B 17/00*  (2006.01)
(52) U.S. Cl.
  CPC ............... *A61F 2002/0852* (2013.01); *A61F 2002/0882* (2013.01)

(56) References Cited

U.S. PATENT DOCUMENTS

| | | |
|---|---|---|
| 3,910,281 A | 10/1975 | Kletschka et al. |
| 4,741,330 A | 5/1988 | Hayhurst |
| 4,750,492 A | 6/1988 | Jacobs |
| 4,898,156 A | 2/1990 | Gatturna et al. |
| 5,041,129 A | 8/1991 | Hayhurst et al. |
| 5,269,809 A | 12/1993 | Hayhurst et al. |
| 5,306,290 A | 4/1994 | Martins et al. |
| 5,306,301 A | 4/1994 | Graf |
| 5,403,348 A | 4/1995 | Bonutti |
| 5,417,691 A | 5/1995 | Hayhurst |
| 5,441,508 A | 8/1995 | Gazielly et al. |
| 5,464,425 A | 11/1995 | Skiba |
| 5,470,337 A | 11/1995 | Moss |
| 5,496,348 A | 3/1996 | Bonutti |
| 5,500,000 A | 3/1996 | Feagin et al. |
| 5,522,846 A | 6/1996 | Bonutti |
| 5,527,343 A | 6/1996 | Bonutti |
| 5,529,075 A | 6/1996 | Clark |
| 5,531,678 A | 7/1996 | Tomba et al. |
| 5,534,012 A | 7/1996 | Bonutti |
| 5,540,718 A | 7/1996 | Bartlett |
| 5,549,617 A | 8/1996 | Green et al. |
| 5,549,630 A | 8/1996 | Bonutti |
| 5,562,689 A | 10/1996 | Green et al. |
| 5,569,305 A | 10/1996 | Bonutti |
| 5,584,862 A | 12/1996 | Bonutti |
| 5,601,571 A | 2/1997 | Moss |
| 5,626,612 A | 5/1997 | Bartlett |
| 5,626,614 A | 5/1997 | Hart |
| 5,647,874 A | 7/1997 | Hayhurst |
| 5,683,418 A | 11/1997 | Luscombe et al. |
| 5,713,921 A | 2/1998 | Bonutti |
| 5,718,717 A | 2/1998 | Bonutti |
| 5,728,100 A | 3/1998 | Skiba |
| 5,733,306 A | 3/1998 | Bonutti |
| 5,769,894 A | 6/1998 | Ferragamo |
| 5,782,862 A | 7/1998 | Bonutti |
| 5,810,848 A | 9/1998 | Hayhurst |
| 5,814,051 A | 9/1998 | Wenstrom |
| 5,814,072 A | 9/1998 | Bonutti |
| 5,814,073 A | 9/1998 | Bonutti |
| 5,845,645 A | 12/1998 | Bonutti |
| 5,897,574 A | 4/1999 | Bonutti |
| 5,921,986 A | 7/1999 | Bonutti |
| 5,928,267 A | 7/1999 | Bonutti et al. |
| 5,941,900 A | 8/1999 | Bonutti |
| 5,948,002 A | 9/1999 | Bonutti |
| 5,954,057 A | 9/1999 | Li |
| 5,961,538 A | 10/1999 | Pedlick et al. |
| 5,964,764 A | 10/1999 | West et al. |
| 5,980,557 A | 11/1999 | Iserin et al. |
| 5,980,559 A | 11/1999 | Bonutti |
| 5,989,282 A | 11/1999 | Bonutti |
| 6,007,567 A | 12/1999 | Bonutti |
| 6,013,083 A | 1/2000 | Bennett |
| 6,033,430 A | 3/2000 | Bonutti |
| 6,045,551 A | 4/2000 | Bonutti |
| 6,056,752 A | 5/2000 | Roger |
| 6,056,772 A | 5/2000 | Bonutti |
| 6,056,773 A | 5/2000 | Bonutti |
| 6,068,648 A | 5/2000 | Cole et al. |
| 6,077,292 A | 6/2000 | Bonutti |
| 6,099,530 A | 8/2000 | Simonian et al. |
| 6,102,934 A | 8/2000 | Li |
| 6,110,183 A * | 8/2000 | Cope ............... A61B 17/0483 606/139 |
| 6,117,160 A | 9/2000 | Bonutti |
| RE36,974 E | 11/2000 | Bonutti |
| 6,152,935 A | 11/2000 | Kammerer et al. |
| 6,152,949 A | 11/2000 | Bonutti |
| 6,156,044 A | 12/2000 | Kammerer et al. |
| 6,221,107 B1 | 4/2001 | Steiner et al. |
| 6,238,395 B1 | 5/2001 | Bonutti |
| 6,270,518 B1 | 8/2001 | Pedlick et al. |
| 6,287,325 B1 | 9/2001 | Bonutti |
| 6,293,961 B2 | 9/2001 | Schwartz et al. |
| 6,306,159 B1 | 10/2001 | Schwartz et al. |
| 6,309,405 B1 | 10/2001 | Bonutti |
| 6,312,448 B1 | 11/2001 | Bonutti |
| 6,319,271 B1 | 11/2001 | Schwartz et al. |
| 6,364,897 B1 | 4/2002 | Bonutti |
| 6,423,080 B1 | 7/2002 | Gellman et al. |
| 6,428,562 B2 | 8/2002 | Bonutti |
| 6,432,123 B2 | 8/2002 | Schwartz et al. |
| 6,451,030 B2 | 9/2002 | Li et al. |
| 6,468,289 B1 | 10/2002 | Bonutti |
| 6,491,714 B1 * | 12/2002 | Bennett ............... A61B 17/1778 606/232 |
| 6,500,195 B2 | 12/2002 | Bonutti |
| 6,517,578 B2 | 2/2003 | Hein |
| 6,527,795 B1 | 3/2003 | Lizardi |
| 6,533,802 B2 | 3/2003 | Bojarski et al. |
| 6,575,987 B2 | 6/2003 | Gellman et al. |
| 6,592,609 B1 | 7/2003 | Bonutti |
| 6,607,534 B2 | 8/2003 | Bonutti |
| 6,635,073 B2 | 10/2003 | Bonutti |
| 6,638,279 B2 | 10/2003 | Bonutti |
| 6,656,182 B1 | 12/2003 | Hayhurst |
| 6,660,022 B1 | 12/2003 | Li et al. |
| 6,726,707 B2 | 4/2004 | Pedlick et al. |
| 6,736,829 B1 | 5/2004 | Li et al. |
| 6,770,076 B2 | 8/2004 | Foerster |
| 6,773,436 B2 | 8/2004 | Donnelly et al. |
| 6,855,157 B2 | 2/2005 | Foerster et al. |
| 6,887,259 B2 | 5/2005 | Lizardi |
| 6,972,027 B2 | 12/2005 | Fallin et al. |
| 6,986,780 B2 | 1/2006 | Rudnick et al. |
| 6,986,781 B2 | 1/2006 | Smith |
| 6,997,305 B2 | 2/2006 | Demarest et al. |
| 6,997,940 B2 | 2/2006 | Bonutti |
| 7,021,316 B2 | 4/2006 | Leiboff |
| 7,033,380 B2 | 4/2006 | Schwartz et al. |
| 7,037,324 B2 | 5/2006 | Martinek |
| 7,041,120 B2 | 5/2006 | Li et al. |
| 7,083,638 B2 | 8/2006 | Foerster |
| 7,128,753 B1 | 10/2006 | Bonutti et al. |
| 7,153,312 B1 | 12/2006 | Torrie et al. |
| 7,217,279 B2 | 5/2007 | Reese |
| 7,232,455 B2 | 6/2007 | Pedlick et al. |
| 7,235,091 B2 | 6/2007 | Thornes |
| 7,320,701 B2 | 1/2008 | Haut et al. |
| 7,390,332 B2 | 6/2008 | Selvitelli et al. |
| 7,455,683 B2 | 11/2008 | Geissler et al. |
| 7,481,825 B2 | 1/2009 | Bonutti |
| 7,530,990 B2 | 5/2009 | Perriello et al. |
| 7,556,640 B2 | 7/2009 | Foerster |
| 7,572,275 B2 | 8/2009 | Fallin et al. |
| 7,621,865 B2 | 11/2009 | Gellman et al. |
| 7,641,672 B2 | 1/2010 | Fallin et al. |
| 7,651,509 B2 | 1/2010 | Bojarski et al. |
| 7,674,275 B2 | 3/2010 | Martin et al. |
| 7,686,838 B2 | 3/2010 | Wolf et al. |
| 7,695,494 B2 | 4/2010 | Foerster |
| 7,758,598 B2 | 7/2010 | Conlon et al. |
| 7,776,077 B2 | 8/2010 | Kaiser et al. |
| 7,780,682 B2 | 8/2010 | Catanese et al. |
| 7,815,655 B2 | 10/2010 | Catanese et al. |
| 7,815,662 B2 | 10/2010 | Spivey et al. |
| 7,819,898 B2 | 10/2010 | Stone et al. |
| 7,837,669 B2 | 11/2010 | Dann et al. |
| 7,846,181 B2 | 12/2010 | Schwartz et al. |
| 7,850,639 B2 | 12/2010 | Rue et al. |
| 7,857,830 B2 | 12/2010 | Stone et al. |
| 7,875,057 B2 | 1/2011 | Cook et al. |
| 7,875,058 B2 | 1/2011 | Holmes, Jr. |
| 7,875,064 B2 | 1/2011 | Donnelly et al. |

(56) References Cited

U.S. PATENT DOCUMENTS

| | | | |
|---|---|---|---|
| 7,879,055 B1 | 2/2011 | Stone et al. |
| 7,887,551 B2 | 2/2011 | Bojarski et al. |
| 7,901,431 B2 | 3/2011 | Shurnas |
| 7,905,904 B2 | 3/2011 | Stone et al. |
| 7,909,851 B2 | 3/2011 | Stone et al. |
| 7,914,542 B2 | 3/2011 | Lamson et al. |
| 7,927,342 B2 | 4/2011 | Rioux |
| 7,951,158 B2 | 5/2011 | Catanese et al. |
| 7,963,966 B2 | 6/2011 | Cole |
| 7,967,843 B2 | 6/2011 | Kaiser et al. |
| 7,998,171 B2 | 8/2011 | Bartlett et al. |
| 8,007,503 B2 | 8/2011 | Catanese et al. |
| 8,043,309 B2 | 10/2011 | Catanese et al. |
| RE43,143 E | 1/2012 | Hayhurst |
| 8,092,366 B2 | 1/2012 | Evans |
| 8,109,965 B2 | 2/2012 | Stone et al. |
| 8,109,967 B2 | 2/2012 | Koyfman et al. |
| 8,133,257 B2 | 3/2012 | Cook et al. |
| 8,142,449 B2 | 3/2012 | Kohl et al. |
| 8,147,514 B2 | 4/2012 | Bonutti |
| 8,162,997 B2 | 4/2012 | Struhl |
| 8,166,978 B2 | 5/2012 | Laufer et al. |
| 8,172,744 B2 | 5/2012 | Gellman et al. |
| 8,182,441 B2 | 5/2012 | Swain et al. |
| 8,182,459 B2 | 5/2012 | Dann et al. |
| 8,187,176 B2 | 5/2012 | Stokes et al. |
| 8,192,450 B2 | 6/2012 | Gonzales et al. |
| 8,202,298 B2 | 6/2012 | Cook et al. |
| 8,211,118 B2 | 7/2012 | Catanese et al. |
| 8,221,454 B2 | 7/2012 | Schaffhausen |
| 8,221,455 B2 | 7/2012 | Shurnas et al. |
| 8,236,011 B2 | 8/2012 | Harris et al. |
| 8,241,305 B2 | 8/2012 | Stone |
| 8,277,459 B2 | 10/2012 | Sand et al. |
| 8,292,921 B2 | 10/2012 | Stone et al. |
| 8,303,604 B2 | 11/2012 | Stone et al. |
| 8,323,315 B2 | 12/2012 | Schwartz et al. |
| 8,323,338 B2 | 12/2012 | Lebeau et al. |
| 8,337,525 B2 | 12/2012 | Stone et al. |
| 8,343,187 B2 | 1/2013 | Lamson et al. |
| 8,348,960 B2 | 1/2013 | Michel et al. |
| 8,366,744 B2 | 2/2013 | Bojarski et al. |
| 8,388,653 B2 | 3/2013 | Nobis et al. |
| 8,394,110 B2 | 3/2013 | Catanese et al. |
| 8,398,678 B2 | 3/2013 | Baker et al. |
| 8,403,943 B2 | 3/2013 | Schwartz et al. |
| 8,425,536 B2 | 4/2013 | Foerster et al. |
| 8,425,554 B2 | 4/2013 | Denove et al. |
| 8,435,253 B2 | 5/2013 | Niese et al. |
| 8,439,976 B2 | 5/2013 | Albertorio et al. |
| 8,444,672 B2 | 5/2013 | Foerster |
| 8,449,584 B2 | 5/2013 | Donnelly et al. |
| 8,460,379 B2 | 6/2013 | Albertorio et al. |
| 8,480,686 B2 | 7/2013 | Bakos et al. |
| 8,491,609 B2 | 7/2013 | Stone |
| 8,496,684 B2 | 7/2013 | Crainich et al. |
| 8,506,597 B2 | 8/2013 | Kaiser et al. |
| 8,512,374 B2 | 8/2013 | Schwartz et al. |
| 8,512,375 B2 | 8/2013 | Torrie et al. |
| 8,512,376 B2 | 8/2013 | Thornes |
| 8,535,377 B2 | 9/2013 | Myers et al. |
| 8,545,558 B2 | 10/2013 | Spenciner et al. |
| 8,551,140 B2 | 10/2013 | Denham et al. |
| 8,562,631 B2 | 10/2013 | Saliman et al. |
| 8,568,449 B2 | 10/2013 | Koyfman et al. |
| 8,579,797 B2 | 11/2013 | Arnal et al. |
| 8,579,975 B2 | 11/2013 | Myers |
| 8,591,578 B2 | 11/2013 | Albertorio et al. |
| 8,602,965 B2 | 12/2013 | Chu et al. |
| 8,603,125 B2 | 12/2013 | Stone et al. |
| 8,617,185 B2 | 12/2013 | Bonutti et al. |
| 8,617,241 B2 | 12/2013 | Myers |
| 8,623,051 B2 | 1/2014 | Bojarski et al. |
| 8,628,573 B2 | 1/2014 | Roller et al. |
| 8,632,569 B2 | 1/2014 | Stone et al. |
| 8,636,641 B2 | 1/2014 | Gellman et al. |
| 8,652,141 B2 | 2/2014 | Rush et al. |
| 8,652,166 B2 | 2/2014 | Aakerfeldt |
| 8,663,243 B2 | 3/2014 | Lamson et al. |
| 8,685,060 B2 | 4/2014 | Foerster |
| 8,696,704 B2 | 4/2014 | Selvitelli et al. |
| 8,702,796 B2 | 4/2014 | Myers |
| 8,708,885 B2 | 4/2014 | Khamis et al. |
| 8,715,298 B2 | 5/2014 | Catanese et al. |
| 8,721,683 B2 | 5/2014 | Graf |
| 8,727,962 B2 | 5/2014 | Gellman et al. |
| 8,740,939 B2 | 6/2014 | Stone et al. |
| 8,753,375 B2 | 6/2014 | Albertorio |
| 8,771,314 B2 | 7/2014 | Crombie et al. |
| 8,771,316 B2 | 7/2014 | Denham et al. |
| 8,784,426 B2 | 7/2014 | Smith et al. |
| 8,790,238 B2 | 7/2014 | Gellman et al. |
| 8,790,239 B2 | 7/2014 | Gellman et al. |
| 8,790,369 B2 | 7/2014 | Orphanos et al. |
| 8,795,293 B2 | 8/2014 | Petersen et al. |
| 8,808,312 B2 | 8/2014 | Rioux |
| 8,808,329 B2 | 8/2014 | Bonutti |
| 8,814,777 B2 | 8/2014 | Gellman et al. |
| 8,814,902 B2 | 8/2014 | Bonutti |
| 8,828,052 B2 | 9/2014 | Caborn et al. |
| 8,834,523 B2 | 9/2014 | Ferragamo et al. |
| 8,834,524 B2 | 9/2014 | Torrie et al. |
| 8,840,644 B2 | 9/2014 | Napolitano et al. |
| 8,840,645 B2 | 9/2014 | Denham et al. |
| 8,852,250 B2 | 10/2014 | Lombardo et al. |
| 8,858,575 B2 | 10/2014 | Rioux |
| 8,870,876 B2 | 10/2014 | Lettmann et al. |
| 8,876,900 B2 | 11/2014 | Guederian et al. |
| 8,882,833 B2 | 11/2014 | Saylor et al. |
| 8,888,798 B2 | 11/2014 | Bourque et al. |
| 8,888,815 B2 | 11/2014 | Holmes, Jr. |
| 8,926,662 B2 | 1/2015 | Perriello et al. |
| 8,936,609 B2 | 1/2015 | Catanese et al. |
| 8,940,001 B2 | 1/2015 | Catanese et al. |
| 8,944,989 B2 | 2/2015 | Weiser et al. |
| 8,944,990 B2 | 2/2015 | Hamel et al. |
| 8,956,318 B2 | 2/2015 | Miller et al. |
| 8,961,575 B2 | 2/2015 | Choinski |
| 8,968,327 B2 | 3/2015 | Klotz et al. |
| 8,979,875 B2 | 3/2015 | Gonzales et al. |
| 8,986,327 B2 | 3/2015 | Karasic et al. |
| 9,005,245 B2 | 4/2015 | Thornes et al. |
| 9,028,547 B2 | 5/2015 | Lebeau et al. |
| 9,039,649 B2 | 5/2015 | Neisz et al. |
| 9,050,168 B2 | 6/2015 | Neisz et al. |
| 9,056,003 B2 | 6/2015 | Demmer et al. |
| 9,060,768 B2 | 6/2015 | Ferragamo et al. |
| 9,060,844 B2 | 6/2015 | Kagan et al. |
| 9,072,509 B2 | 7/2015 | Stoll et al. |
| 9,072,510 B2 | 7/2015 | Thornes et al. |
| 9,101,461 B2 | 8/2015 | Albertorio et al. |
| 9,107,701 B2 | 8/2015 | Cole |
| 9,173,651 B2 | 11/2015 | Stone et al. |
| 9,173,653 B2 | 11/2015 | Bojarski et al. |
| 9,265,495 B2 | 2/2016 | Petersen et al. |
| 9,445,806 B2 | 9/2016 | Hart et al. |
| 10,653,409 B2 * | 5/2020 | Triplett ................ A61F 2/0805 |
| 2001/0014825 A1 | 8/2001 | Burke et al. |
| 2002/0019649 A1 | 2/2002 | Sikora et al. |
| 2003/0236555 A1 | 12/2003 | Thornes |
| 2004/0010287 A1 | 1/2004 | Bonutti |
| 2004/0015171 A1 | 1/2004 | Bojarski et al. |
| 2005/0049636 A1 | 3/2005 | Leiboff |
| 2005/0125030 A1 * | 6/2005 | Forsberg ............ A61B 17/0057 |
| | | 606/213 |
| 2005/0288694 A1 | 12/2005 | Solomon |
| 2006/0116718 A1 | 6/2006 | Leiboff |
| 2006/0155375 A1 | 7/2006 | Kagan et al. |
| 2006/0178702 A1 | 8/2006 | Pierce et al. |
| 2006/0229671 A1 | 10/2006 | Steiner et al. |
| 2006/0271060 A1 | 11/2006 | Gordon |
| 2007/0083236 A1 | 4/2007 | Sikora et al. |
| 2007/0112338 A1 | 5/2007 | Cohen et al. |
| 2008/0021485 A1 | 1/2008 | Catanese et al. |

(56) References Cited

U.S. PATENT DOCUMENTS

| | | |
|---|---|---|
| 2008/0039872 A1 | 2/2008 | Catanese et al. |
| 2008/0039875 A1 | 2/2008 | Catanese et al. |
| 2008/0039894 A1 | 2/2008 | Catanese et al. |
| 2008/0058816 A1 | 3/2008 | Philippon et al. |
| 2008/0071297 A1* | 3/2008 | Kohl ................ A61B 17/0401 606/151 |
| 2008/0077182 A1 | 3/2008 | Geissler et al. |
| 2008/0103527 A1 | 5/2008 | Martin et al. |
| 2008/0125791 A1 | 5/2008 | Gellman et al. |
| 2008/0140116 A1 | 6/2008 | Bonutti |
| 2008/0188935 A1 | 8/2008 | Saylor et al. |
| 2008/0208204 A1 | 8/2008 | Schmieding et al. |
| 2008/0287991 A1 | 11/2008 | Fromm |
| 2009/0043318 A1 | 2/2009 | Michel et al. |
| 2009/0112234 A1 | 4/2009 | Crainich et al. |
| 2009/0118762 A1 | 5/2009 | Crainch et al. |
| 2009/0209804 A1 | 8/2009 | Seiler et al. |
| 2009/0228042 A1 | 9/2009 | Koogle et al. |
| 2009/0312792 A1 | 12/2009 | Fallin et al. |
| 2010/0114161 A1 | 5/2010 | Bojarski et al. |
| 2010/0114162 A1 | 5/2010 | Bojarski et al. |
| 2010/0130989 A1 | 5/2010 | Bourque et al. |
| 2010/0160963 A1 | 6/2010 | Fallin et al. |
| 2010/0204731 A1 | 8/2010 | Hart et al. |
| 2010/0249835 A1 | 9/2010 | Schwartz et al. |
| 2010/0262185 A1 | 10/2010 | Gelfand et al. |
| 2010/0298817 A1 | 11/2010 | Gellman et al. |
| 2011/0257664 A1* | 10/2011 | Cauthen, III ...... A61B 17/0401 606/144 |
| 2012/0053504 A1 | 3/2012 | Kagan et al. |
| 2012/0123416 A1 | 5/2012 | Gelfand et al. |
| 2012/0123474 A1 | 5/2012 | Zajac et al. |
| 2012/0130492 A1 | 5/2012 | Eggli et al. |
| 2012/0150203 A1 | 6/2012 | Brady et al. |
| 2012/0180291 A1 | 7/2012 | Oren et al. |
| 2012/0203250 A1 | 8/2012 | Weir et al. |
| 2012/0239086 A1 | 9/2012 | Reznik et al. |
| 2012/0245633 A1 | 9/2012 | Schlotterback et al. |
| 2012/0283835 A1* | 11/2012 | Bentley ................ A61N 1/0558 623/17.16 |
| 2012/0290002 A1 | 11/2012 | Astorino |
| 2013/0006303 A1 | 1/2013 | Petersen et al. |
| 2013/0035720 A1 | 2/2013 | Perriello et al. |
| 2013/0046319 A1 | 2/2013 | Arnett et al. |
| 2013/0072989 A1 | 3/2013 | Overes et al. |
| 2013/0079665 A1 | 3/2013 | Hibner et al. |
| 2013/0096612 A1 | 4/2013 | Zajac et al. |
| 2013/0096613 A1 | 4/2013 | Hart et al. |
| 2013/0096678 A1 | 4/2013 | Denham |
| 2013/0103057 A1 | 4/2013 | Keating et al. |
| 2013/0103085 A1 | 4/2013 | Hart et al. |
| 2013/0123810 A1 | 5/2013 | Brown et al. |
| 2013/0123841 A1 | 5/2013 | Lyon |
| 2013/0138108 A1 | 5/2013 | Dreyfuss et al. |
| 2013/0138123 A1 | 5/2013 | Stone et al. |
| 2013/0138150 A1 | 5/2013 | Baker et al. |
| 2013/0144314 A1 | 6/2013 | Bojarski et al. |
| 2013/0172944 A1 | 7/2013 | Fritzinger et al. |
| 2013/0184708 A1 | 7/2013 | Robinson et al. |
| 2013/0204276 A1 | 8/2013 | Stone et al. |
| 2013/0211452 A1 | 8/2013 | Stone et al. |
| 2013/0218176 A1 | 8/2013 | Denove et al. |
| 2013/0238039 A1 | 9/2013 | Bonutti |
| 2013/0268000 A1 | 10/2013 | Harner et al. |
| 2013/0268073 A1 | 10/2013 | Albertorio et al. |
| 2013/0304120 A1 | 11/2013 | Stone et al. |
| 2013/0317544 A1 | 11/2013 | Ferguson et al. |
| 2013/0324905 A1 | 12/2013 | Nelson et al. |
| 2013/0324907 A1 | 12/2013 | Huntley et al. |
| 2013/0324926 A1 | 12/2013 | Nelson et al. |
| 2013/0331759 A1 | 12/2013 | Neisz et al. |
| 2013/0331886 A1 | 12/2013 | Thornes |
| 2013/0345751 A1 | 12/2013 | Beck |
| 2014/0005473 A1 | 1/2014 | Catanese et al. |
| 2014/0074239 A1 | 3/2014 | Albertorio et al. |
| 2014/0081399 A1 | 3/2014 | Roller et al. |
| 2014/0088646 A1 | 3/2014 | Wales et al. |
| 2014/0094912 A1 | 4/2014 | Walker |
| 2014/0121674 A1 | 5/2014 | Staunton |
| 2014/0135835 A1 | 5/2014 | Stone et al. |
| 2014/0180313 A1 | 6/2014 | Harrison et al. |
| 2014/0188245 A1 | 7/2014 | Neisz et al. |
| 2014/0194907 A1 | 7/2014 | Bonutti et al. |
| 2014/0194933 A1 | 7/2014 | Bonutti |
| 2014/0207159 A1 | 7/2014 | Miller et al. |
| 2014/0214152 A1 | 7/2014 | Bielefeld |
| 2014/0222148 A1 | 8/2014 | Shinde |
| 2014/0257294 A1 | 9/2014 | Gedet et al. |
| 2014/0257346 A1 | 9/2014 | Sengun et al. |
| 2014/0257380 A1 | 9/2014 | Bonutti |
| 2014/0276333 A1 | 9/2014 | Neisz et al. |
| 2014/0296910 A1 | 10/2014 | Graf |
| 2014/0309689 A1 | 10/2014 | Sikora et al. |
| 2014/0324101 A1 | 10/2014 | Denham et al. |
| 2014/0330378 A1 | 11/2014 | Smith et al. |
| 2014/0336451 A1 | 11/2014 | Gellman et al. |
| 2014/0350599 A1 | 11/2014 | Torrie et al. |
| 2015/0018745 A1 | 1/2015 | Neisz et al. |
| 2015/0039026 A1 | 2/2015 | Pasquali et al. |
| 2015/0039031 A1 | 2/2015 | Sikora et al. |
| 2015/0057750 A1 | 2/2015 | Timmerman |
| 2015/0073477 A1 | 3/2015 | Holmes, Jr. |
| 2015/0094763 A1 | 4/2015 | Ferragamo et al. |
| 2015/0112385 A1 | 4/2015 | Perriello et al. |
| 2015/0112446 A1 | 4/2015 | Melamed et al. |
| 2015/0133941 A1 | 5/2015 | Saylor et al. |
| 2015/0134000 A1 | 5/2015 | Denham et al. |
| 2015/0142052 A1 | 5/2015 | Koogle et al. |
| 2015/0150552 A1 | 6/2015 | Lebeau et al. |
| 2015/0157313 A1 | 6/2015 | Gonzales et al. |
| 2015/0164498 A1 | 6/2015 | Dreyfuss et al. |
| 2015/0173738 A1 | 6/2015 | Schmieding |
| 2015/0216542 A1 | 8/2015 | Libby et al. |
| 2015/0223927 A1 | 8/2015 | Ferragamo et al. |
| 2015/0282804 A1 | 10/2015 | Bonutti et al. |
| 2015/0282849 A1 | 10/2015 | Zeetser et al. |
| 2015/0313655 A1 | 11/2015 | Zeetser et al. |
| 2015/0374358 A1 | 12/2015 | Suzuki et al. |

FOREIGN PATENT DOCUMENTS

| | | |
|---|---|---|
| WO | 2011/040917 A1 | 4/2011 |
| WO | 2011/146340 A1 | 11/2011 |
| WO | 2012/031007 A1 | 3/2012 |
| WO | 2012/040627 A1 | 3/2012 |
| WO | 2012/047925 A2 | 4/2012 |
| WO | 2012/095868 A2 | 7/2012 |
| WO | 2012/109453 A1 | 8/2012 |
| WO | 2012/109455 A1 | 8/2012 |
| WO | 2012/154922 A2 | 11/2012 |
| WO | 2013/019485 A1 | 2/2013 |
| WO | 2013/032435 A1 | 3/2013 |
| WO | 2014/107674 A1 | 7/2014 |
| WO | 2014/137557 A1 | 9/2014 |

OTHER PUBLICATIONS

Comprehensive Solutions for Forefoot and Midfood Sungery using the Mini TightRope System, Arthrex, Inc., www arthrex com 2012, 15 pp.

Comprehensive Solutions for Forefoot and Midfoot Surgery Using the Mini TightRope System, Arthrex, Inc., www.arthrex.com, 2008, 13 pp.

Distal Extremities Orthopaedic Update, Arthrex, Inc., www.arthrex.com, 2014, 24 pp.

Foot & Ankle Repair and Reconstruction Technology Brochure, Arthrex, Inc., www.athrex.com, 2016, 86 pp.

Foot and Ankle Restoration System—Y-Knot 12mm All-Suture Anchor, ConMed Linvatec, www.linvatec.com, 2013, 4 pp.

Lisfranc TightRope Fixation Surgical Technique, Arthrex, Inc., www.arthrex.com, 2013, 6 pp.

(56) References Cited

OTHER PUBLICATIONS

Mini TightRope CMC—Surgical Technique, Arthrex, Inc., www.arthrex.com, 2014, 8 pp.
Small Joint Anchors with Orthocord, DePuy Mitek, 2007, 12 pp.
Supplementary European Search Report dated Jul. 12, 2019 for corresponding European Patent Application No. EP16871284.
The Next Generation in Foot & Ankle Repair and Reconstruction Technology 2016, Arthrex, Inc., www.arthrex.com, 2016, 76 pp.

* cited by examiner

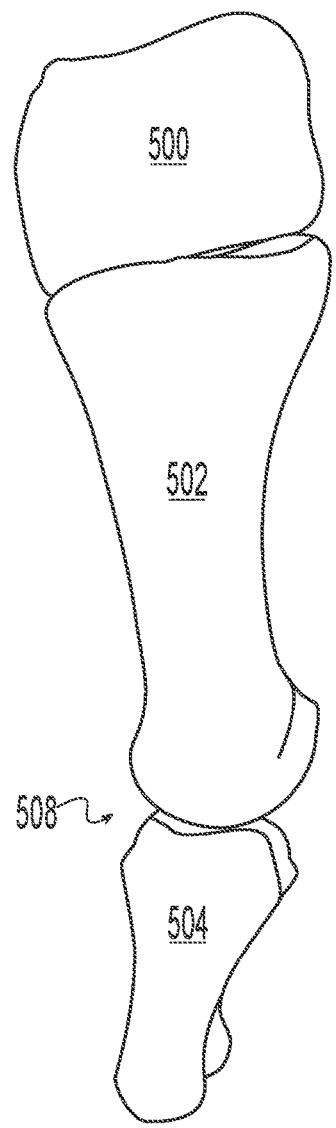
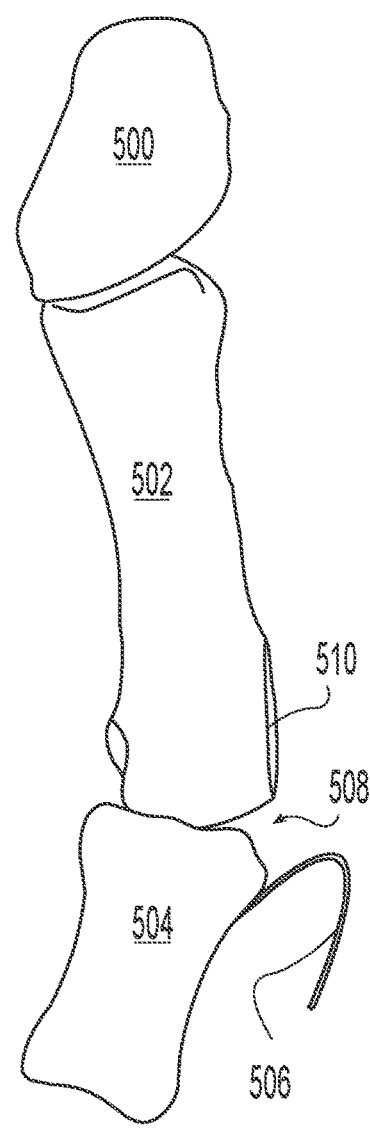
Fig. 14  Fig. 15  Fig. 16

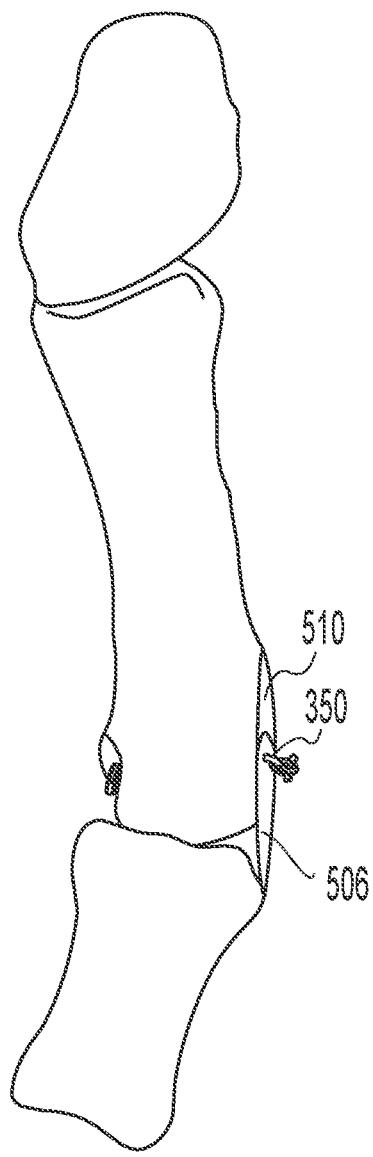
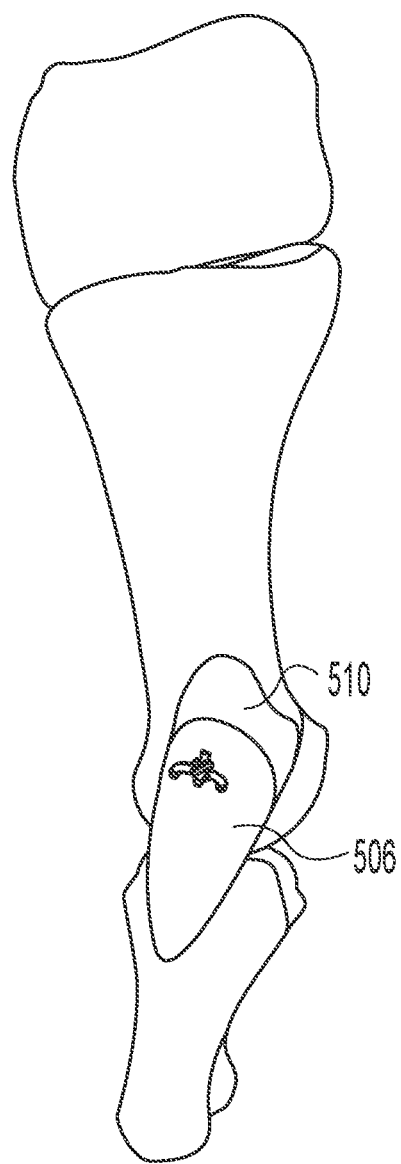
Fig. 23
Fig. 24

DEVICES AND METHODS FOR ANCHORING TISSUE

CROSS-REFERENCE TO RELATED APPLICATIONS

This application is a continuation of U.S. patent application Ser. No. 15/357,197 filed on Nov. 21, 2016, which claims the benefit of U.S. Provisional Application No. 62/263,250, filed Dec. 4, 2015, which are hereby incorporated by reference in their entirety.

FIELD OF THE INVENTION

Examples of the present invention relate generally to devices and methods for anchoring soft tissue, tissue grafts, and the like to a bone.

BACKGROUND

Various conditions may affect skeletal joints such as the deterioration, elongation, shortening, or rupture of soft tissues, cartilage, and/or bone associated with the joint and consequent laxity, pain, and/or deformity. It may be desirable to change the angular alignment of a bone or a portion of a bone to restore function and/or reduce pain. In such a medical procedure it may be necessary to affix soft tissue or a tissue graft to a bone. For example, in a medical procedure to correct an angular deformity of a first ray of a human foot, e.g. hallux valgus, it is often desirable to surgically remove a protruding bone portion or bunion in a procedure known as a bunionectomy adjacent the metatarsophalangeal (MTP) joint. To gain exposure to the surgical site, soft tissues surrounding the joint and the bunion are cut and dissected away. Often these tissues are not reattached for lack of workable devices and methods. Devices and methods to reattach such tissues to provide an anatomic repair are needed.

SUMMARY

The present invention provides devices and methods for anchoring soft tissue, tissue grafts, and the like to a bone. In one example an assembly includes a suture anchor, suture, and inserter. In another example, a method provides for reattaching soft tissue to a bone.

BRIEF DESCRIPTION OF THE DRAWINGS

Various examples of the present invention will be discussed with reference to the appended drawings. These drawings depict only illustrative examples of the invention and are not to be considered limiting of its scope.

FIG. 14 is a medial view of the cuneiform, metatarsal, and proximal phalanx bones of the first ray of a human foot;

FIG. 15 is a dorsal view of the cuneiform, metatarsal, and proximal phalanx bones of the first ray of a human foot;

FIG. 16 is a dorsal view similar to FIG. 15 illustrating a bunionectomy according to an example of the invention; and FIGS. 17-24 illustrate a method of using the assembly of FIG. 1 to anchor soft tissue according to an example of the invention.

DESCRIPTION OF THE ILLUSTRATIVE EXAMPLES

The following illustrative examples describe methods, implants, and instruments for connecting soft tissue to bone. The use of the illustrative devices and methods is illustrated to attach soft tissue detached in conjunction with a bunionectomy during a corrective procedure performed on a first ray of a human foot. In particular the illustrative devices and methods are illustrated to reattach capsular tissue adjacent to an MTP joint. The inventive devices and methods may be used to attach tissue at other locations in the body.

The terms "suture" and "suture strand" are used herein to mean any flexible member, natural or synthetic, useful in a surgical procedure and that are easily flexed. Examples include polymer sutures, wires, surgical tapes, tissue derived strands, and other suitable flexible strands or members. Sutures may be monofilament or multi-filament structures. The term "transverse" is used herein to mean crossing as in non-parallel. The term "tissue" is used herein to mean a patient's body tissue as well as a tissue graft which may be allograft, xenograft, or synthetic.

Figure 4:
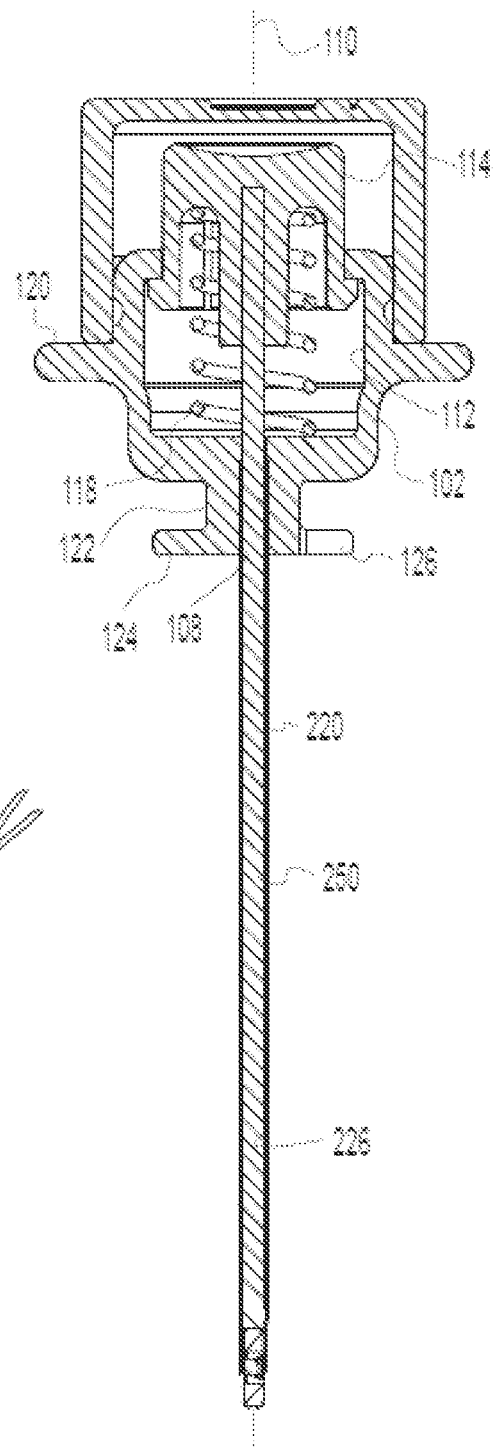
FIG. 4 is a section view of the assembly of FIG. 1 taken along line 4-4 of FIG. 3 with the suture omitted for clarity.
Figure 5:
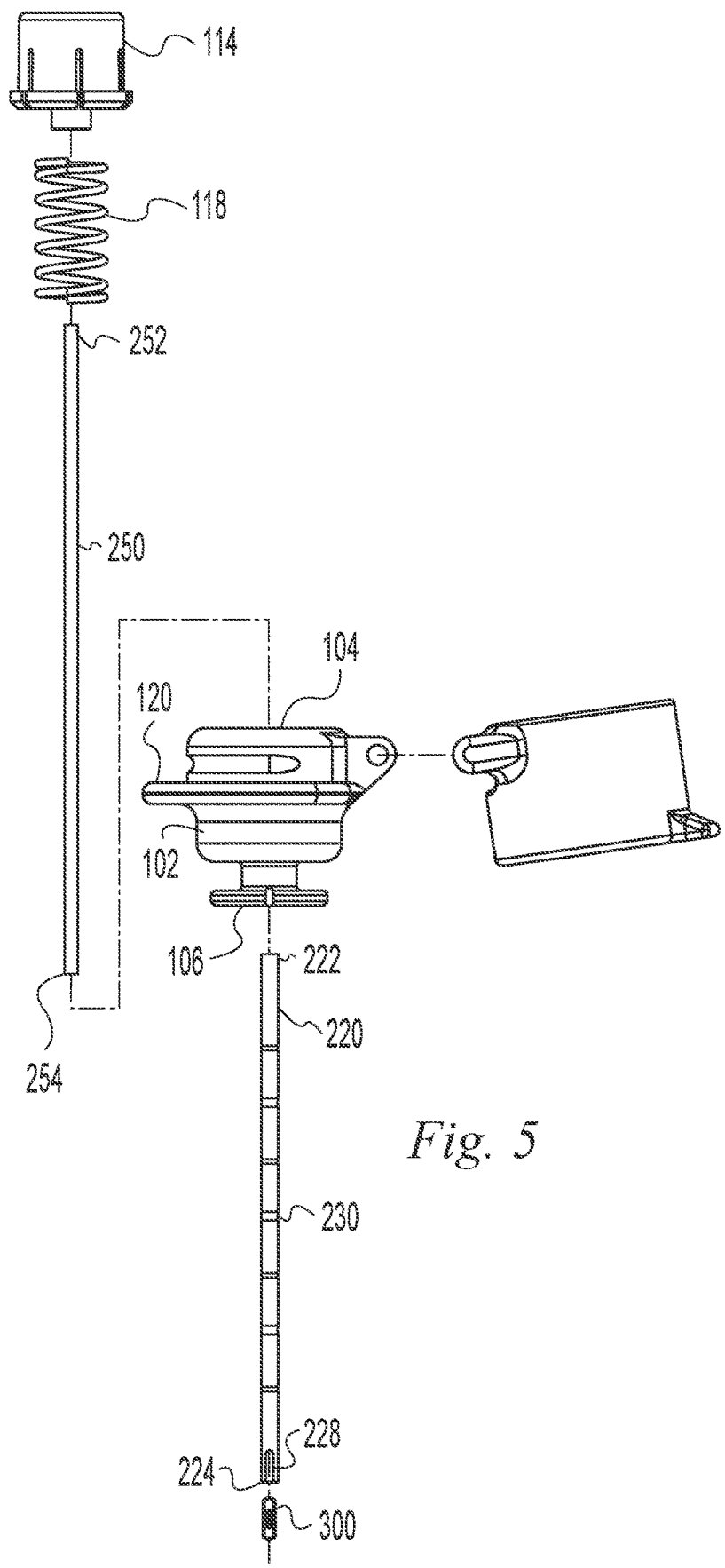
FIG. 5 is an exploded view of the assembly of FIG. 1 with the suture omitted for clarity.

FIGS. 1-5 illustrate an example of a suture anchor assembly 100 according to the present invention. The suture anchor assembly 100 includes a base member 102 having a proximal end 104 and a distal end 106 (FIG. 5). A bore 108 extends through the base member 102 from the distal end 106 to the proximal end 104 and defines a longitudinal axis 110 (FIG. 4). A cavity 112 is formed in a proximal portion of the base member 102 and is enlarged radially relative to the bore 108. An actuator in the form of a push button 114 is mounted in the cavity for axial translation between a first position in which it extends proximally from the cavity and abuts a shoulder adjacent the distal end of the cavity 112 and a second position distal to the first position. A spring 118 biases the button 114 into the first position. The base member 102 includes a radial projection in the form of a flange 120. With one or more fingers positioned distal to the flange 120 and a thumb positioned proximal to the button 114, a user can easily press the button by moving the thumb and fingers together. The base member further includes a trunnion 122 about which suture may be wound. The trunnion 122 includes a distal flange 124 to prevent wound suture from slipping distally off of the trunnion 122. A notch 126 is formed radially in the flange to allow a suture to pass from the trunnion distally. Suture may be wound around the trunnion 122 and then passed through the notch to secure the suture to the base member. A safety device is used to block operation of the pushbutton 114. In the illustrative example of FIGS. 1-5, the safety device is a cap 130 that may be moved by a user from a safe position (FIG. 1) in which it prevents the user from pressing the button 114 to a delivery position (FIG. 2) in which it allows the user to press the button 114. With the cap 130 in the safe position a user can grip the assembly with a thumb on the cap 130 and manipulate the assembly without risk of prematurely pressing the button 114. With the cap 130 in the delivery position a user can easily access the button 114 and press it. In the illustrative example of FIGS. 1-5, the cap 130 is hinged to the base member so that it may be moved without becoming detached from the base member. By remaining attached to the base member, the cap does not need to be separately accounted for by the surgical staff.

A delivery tube 220 is fixed within the bore 108 and extends from the distal end 106 of the base member 102. The delivery tube 220 has a proximal end 222, a distal end 224, and a longitudinal passage 226. The delivery tube 220 includes a slot 228 in the sidewall of the delivery tube adjacent the distal end 224 of the delivery tube. The slot 228 communicates through the sidewall to the longitudinal passage 226 and is open at the distal end 224. The outer surface of the delivery tube 220 includes a plurality of reference marks 230 indicating a plurality of length increments. In the illustrative example of FIGS. 1-5, the reference marks are spaced 5 mm apart with the first reference mark being 5 mm from the proximal end of the slot 228. Every other mark is wider than the prior mark to indicate increments of 10 mm. In the illustrative example of FIGS. 1-5, the delivery tube 220 is sized for delivering a suture anchor to a bone of a human foot and preferably has a diameter of 2-3 mm and a length of 30-60 mm. More preferably the delivery tube 220 has a diameter of 2.4 mm.

An ejector in the form of a push rod 250 has a proximal end 252 and a distal end 254. The push rod 250 is positioned within the delivery tube 220 for axial translation between a first position in which the distal end 254 of the ejector is proximal to the distal end 224 of the delivery tube and a second position in which the distal end 254 of the ejector is distal to the first position. The proximal end 252 of the ejector is fixed to the pushbutton 114 and moves with the pushbutton 114 between the first and second positions.

A suture anchor 300 is positioned in the delivery tube 220 distal to the pushrod 250. The suture anchor is best illustrated in FIGS. 7-13. The suture anchor 300 includes a generally rectangular body 302 having one or more holes through the body for receiving one or more suture strands. In the illustrative example of FIGS. 7-13, the suture anchor includes a pair of parallel holes 304 extending through the body 302 from a first side 306 to a second opposite side 308. The second side 308 includes a groove 310 extending between the holes 304 to receive a suture 350 (FIG. 13) extending through the holes 304. With the suture 350 extending into one hole 304, along the groove 310, and out the other hole 304, the suture is contained in the groove 310 to reduce the overall thickness of the suture anchor and suture assembly. Referring back to FIGS. 1-3, the suture anchor 300 is placed in the distal end of the delivery tube, the suture is passed through the slot 228, through the notch 126, and is then wound around the trunnion 122. In the illustrative example of FIGS. 7-13, the suture anchor is sized for use in bones of a human foot and preferably has a width of 1.5-4 mm and a length of 4-8 mm. More preferably the suture anchor has a width of 2 mm and a length of 6.5 mm. The illustrative suture anchor has a pair of holes sized to receive a single strand of 2-0 high strength suture. Additional holes and holes of different sizes may be provided to receive more strands of suture and/or larger or smaller sutures. For example, 4 holes may be provided to receive 2 strands of suture. The suture ends may have needles attached. The suture anchor may be formed of any suitable material such as for example PEEK, stainless steel, titanium alloys, and resorbable materials.

A suture reservoir may be provided to hold an additional portion of the suture. For example, the suture reservoir may include a body having a circumference greater than that of the trunnion 122 so that an additional length of the suture may be wound around the reservoir body with fewer wraps than would be required for the trunnion. In the illustrative example of FIGS. 1-5, the suture reservoir is in the form of a flat card-like member 360 having a tab 362 extending from one end and positionable under the cap 130. When the cap is in the safe position it traps the tab to retain the member 360 on the base member 102. When the cap is in the delivery position the tab may be removed from under the cap and the member 360 separated from the base member. In the illustrative example of FIGS. 1-5 the tab inserts through a gap between opposed pivots of a cap hinge assembly 364.

Figure 6:
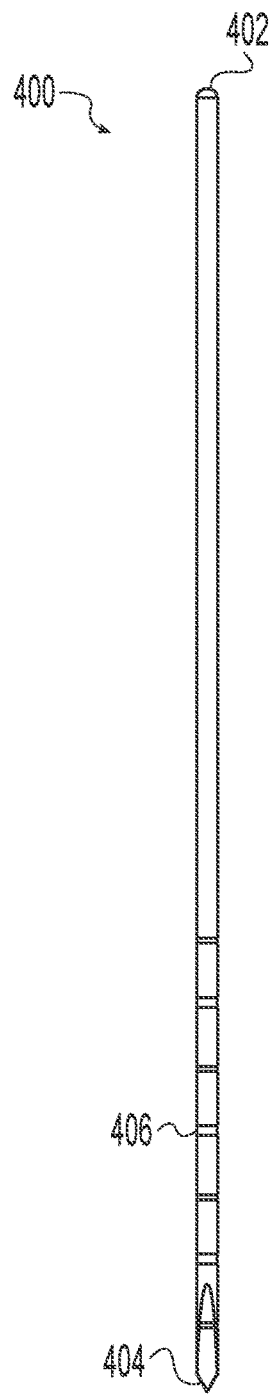
FIG. 6 is a side elevation view of an illustrative example of a hole forming device according to an example of the present invention.
Figure 7:
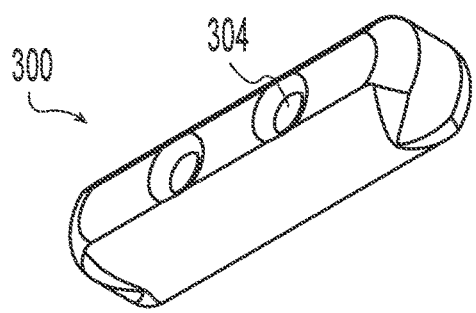
FIG. 7 is a perspective view of the suture anchor of the assembly of FIG. 1.
Figure 8:
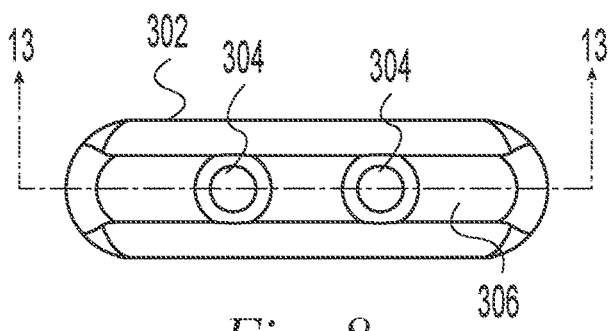
FIG. 8 is a top plan view of the suture anchor of the assembly of FIG. 1.
Figure 9:
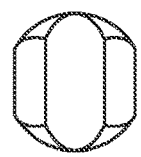
FIG. 9 is a side elevation view of the suture anchor of the assembly of FIG. 1.
Figure 10:
FIG. 10 is a front elevation view of the suture anchor of the assembly of FIG. 1.
Figure 11:
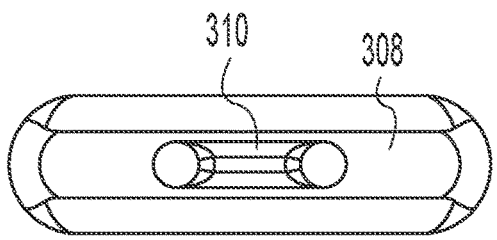
FIG. 11 is a bottom plan view of the suture anchor of the assembly of FIG. 1.
Figure 12:
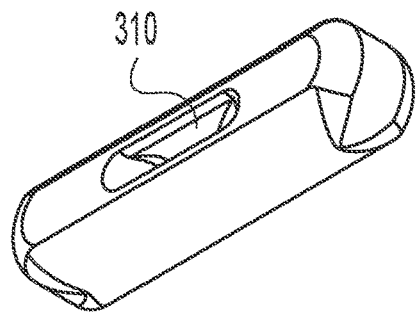
FIG. 12 is a perspective view of the suture anchor of the assembly of FIG. 1.
Figure 13:
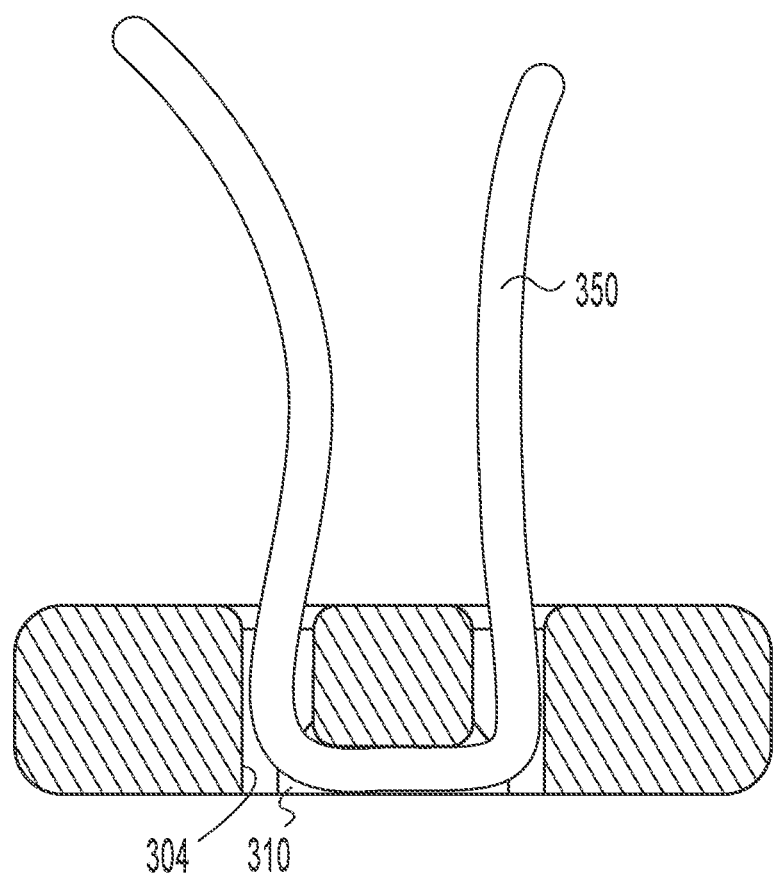
FIG. 13 is a sectional view of the suture anchor of the assembly of FIG. 1 taken along line 13-13 of FIG. 8 and showing a suture routed through the suture anchor.

Referring to FIG. 6, a hole forming instrument may be provided in a diameter suitable for forming a hole for insertion of the delivery tube 220 and anchor 300 into a bone. The hole forming instrument may be a punch, drill, wire or other suitable member. In the illustrative example of FIG. 6, the hole forming instrument is a k-wire 400 having an elongate shaft extending between a proximal end 402 and a distal end 404. A diamond tip is formed at the distal end 404. The k-wire 400 is sized to form a hole slightly larger than the delivery tube 220 diameter. For example, for a 2.4 mm diameter delivery tube, the k-wire is sized to form a 2.5 mm diameter hole. The k-wire 400 includes indicia in the form of reference marks 406 indicating a plurality of length increments and corresponding to the reference marks 230 on the delivery tube 220. In the illustrative example of FIG. 6, the reference marks are spaced 5 mm apart with the first reference mark being 5 mm from the distal end of the k-wire 400. Every other mark is wider than the prior mark to indicate increments of 10 mm. The k-wire 400 may be driven by a wire driver, drill, or other suitable device to form a hole in a bone.

Figure 1:
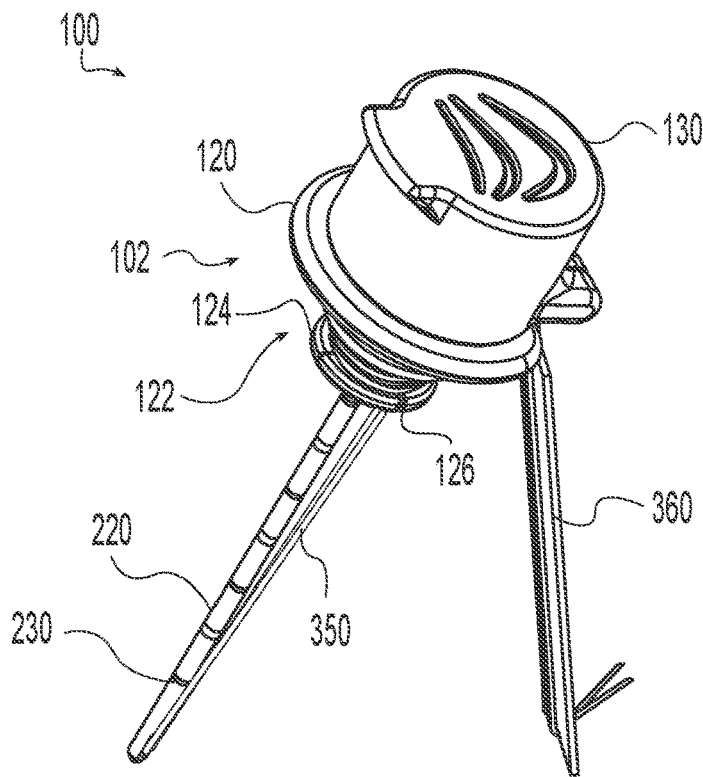
FIG. 1 is a perspective view of an illustrative example of an assembly according to an example of the present invention.
Figure 2:
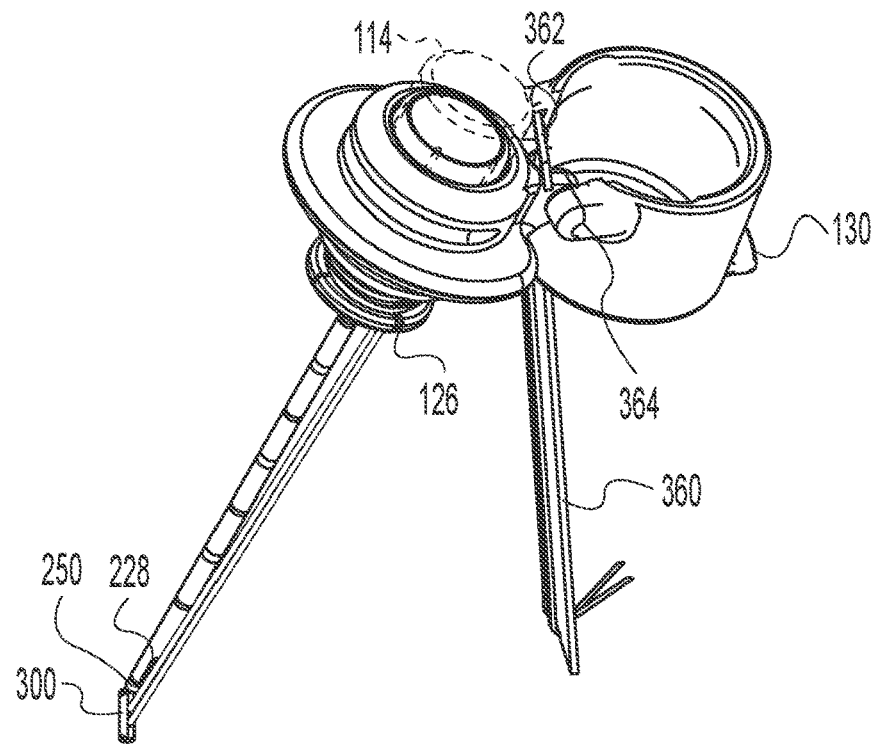
FIG. 2 is a perspective view of the assembly of FIG. 1 showing a different operative state of the assembly.
Figure 3:
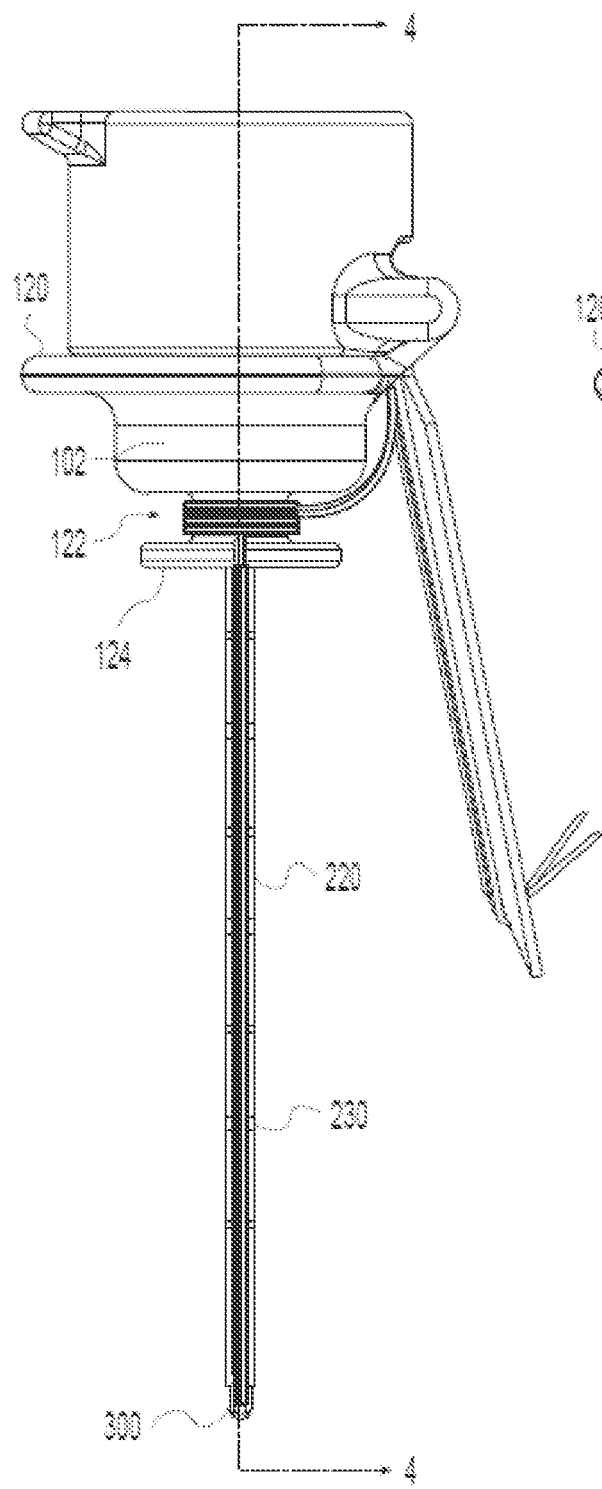
FIG. 3 is a side elevation view of the assembly of FIG. 1.

In use, the k-wire 400 is used to form a hole into a bone from a proximal bone surface to a distal bone surface. The depth of the hole may be determined by reading the reference marks 406 on the k-wire shaft relative to the proximal bone surface. The k-wire may then be removed and the suture anchor assembly 100 may be used to position the anchor 300. With the cap 130 in the safe position a user can grip the assembly with a thumb on the cap 130 and manipulate the assembly without risk of prematurely pressing the button 114 and ejecting the anchor 300. The anchor 300 and delivery tube 220 may be inserted into the hole formed by the k-wire 400. Preferably the delivery tube 220 is inserted to an indicated depth corresponding to the indicated depth of the hole formed by the k-wire 400. Due to the reference marks 230 of the delivery tube 220 being offset from the distal end 224 of the delivery tube 220 by the length of the slot 228, the delivery tube 220 will extend through the bone hole further than the k-wire by a distance equal to the slot length. This ensures that the anchor 300 will have room beyond the distal bone surface to rotate out of the end of the delivery tube 220 without the tube extending unnecessarily far. Once the delivery tube 220 is positioned, the safety cap 130 is flipped open and the button 114 is depressed (FIG. 2). As the push rod 250 presses the anchor 300 out of the distal end of the delivery tube 220, tension in the suture portion extending between the trunnion 122 and the anchor 300 causes the anchor 300 to pivot into a deployed position.

FIG. 14 illustrates a medial view of cuneiform 500, metatarsal 502, and proximal phalangeal 504 bones of a human foot while FIG. 15 illustrates a dorsal view of the same bones. In the illustrative example of FIGS. 14-15, the bones are in the first ray of a human foot on which a bunion corrective procedure is to be performed.

FIGS. 16-24 illustrate a surgical procedure utilizing the illustrative examples of FIGS. 1-13. In FIG. 16, soft tissue 506 adjacent the metatarsophalangeal (MTP) joint 508, e.g. capsular tissue extending between the metatarsal and phalangeal bones, has been dissected away from the metatarsal bone 502. A bunionectomy has been performed to remove a protruding bone portion, e.g. a bunion, on the medial side of the metatarsal bone 502 leaving a decorticated region 510. The decorticated region 510, with its lack of a cortical outer layer, has little strength to support a traditional bone anchor.

Figure 17:
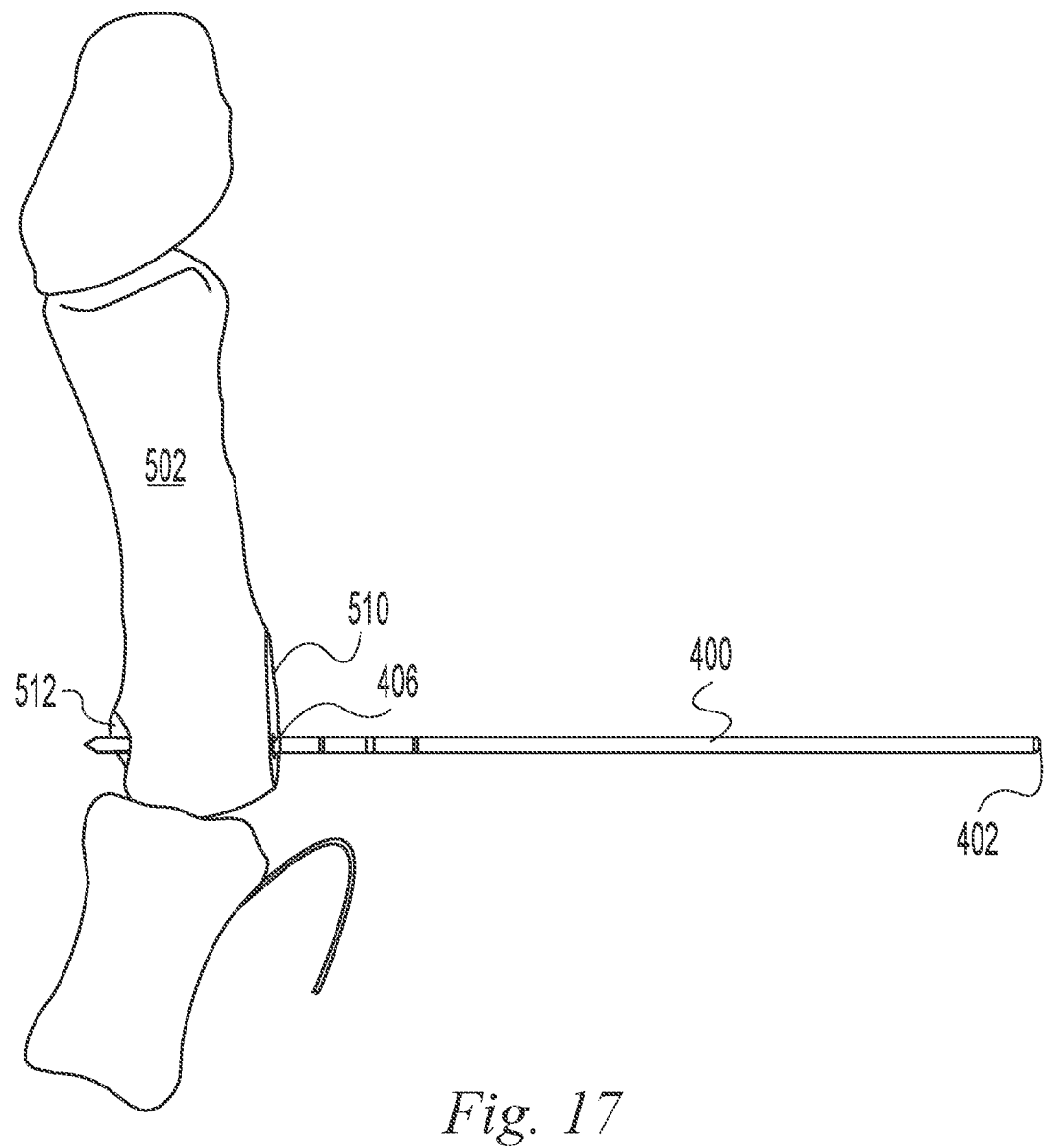

In FIG. 17, the k-wire 400 of FIG. 6 has been driven into the decorticated region 510, across the metatarsal bone 502, and out through the cortical bone 512 opposite the decorticated region 510. The insertion depth of the k-wire is noted by reading the reference marks 406 on the k-wire shaft relative to the proximal bone surface. In the illustrative example of FIG. 17, the k-wire has been driven to the fourth reference mark from the proximal end of the k-wire.

Figure 18:
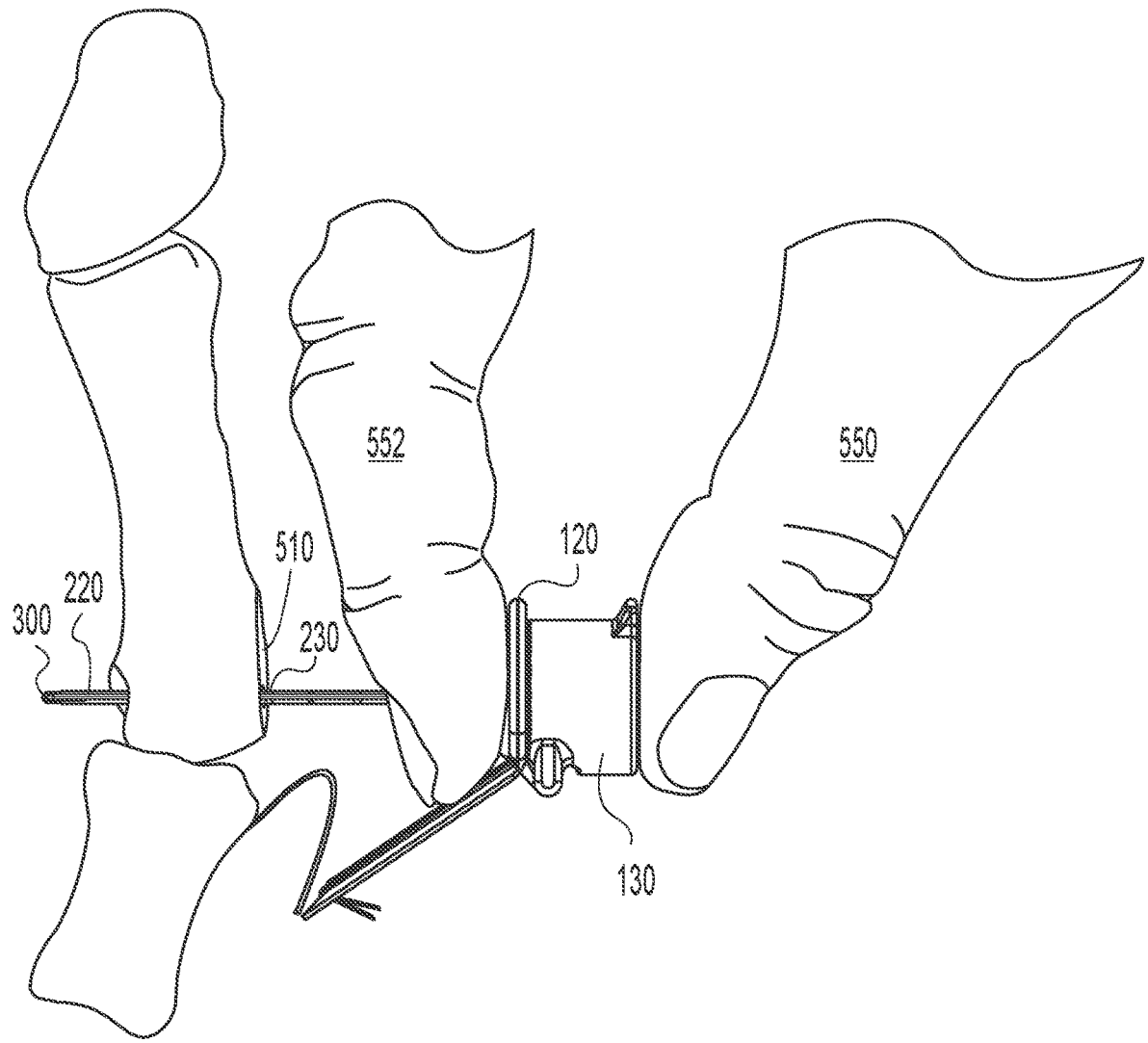

In FIG. 18, the k-wire has been removed and the suture anchor 300 and delivery tube 220 are inserted into the hole formed by the k-wire 400. The user's thumb 550 and at least one finger 552 grip the cap 130 and flange 120 and are used to manipulate the assembly 100 as needed. The delivery tube is inserted until the fourth reference mark 230 as measured from the proximal end of the delivery tube is aligned with the proximal bone surface of the decorticated region 510 corresponding to the k-wire indicated depth.

Figure 19:
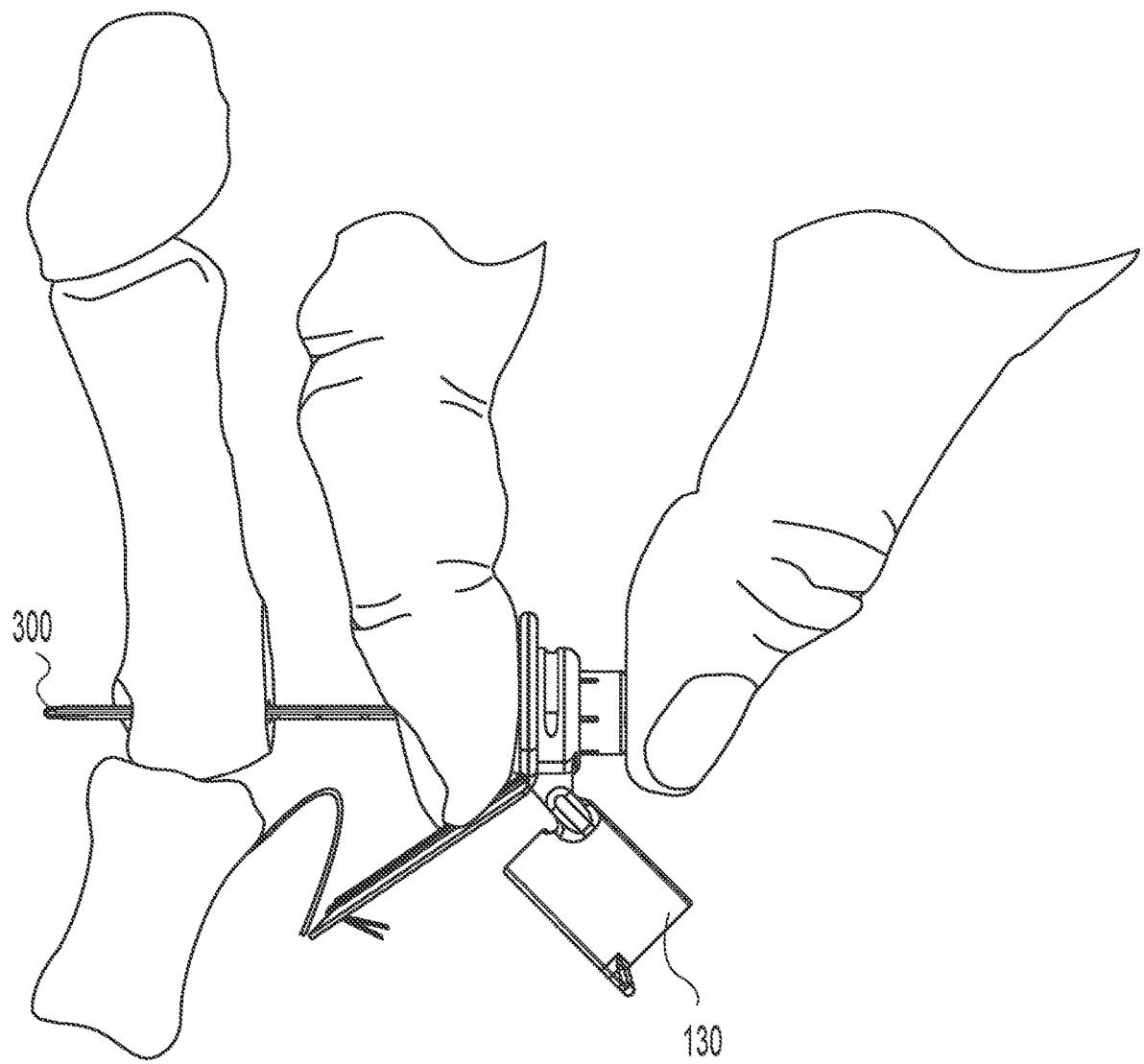

In FIG. 19, the safety cap 130 has been flipped open to arm the assembly 100 for deploying the anchor 300.

Figure 20:
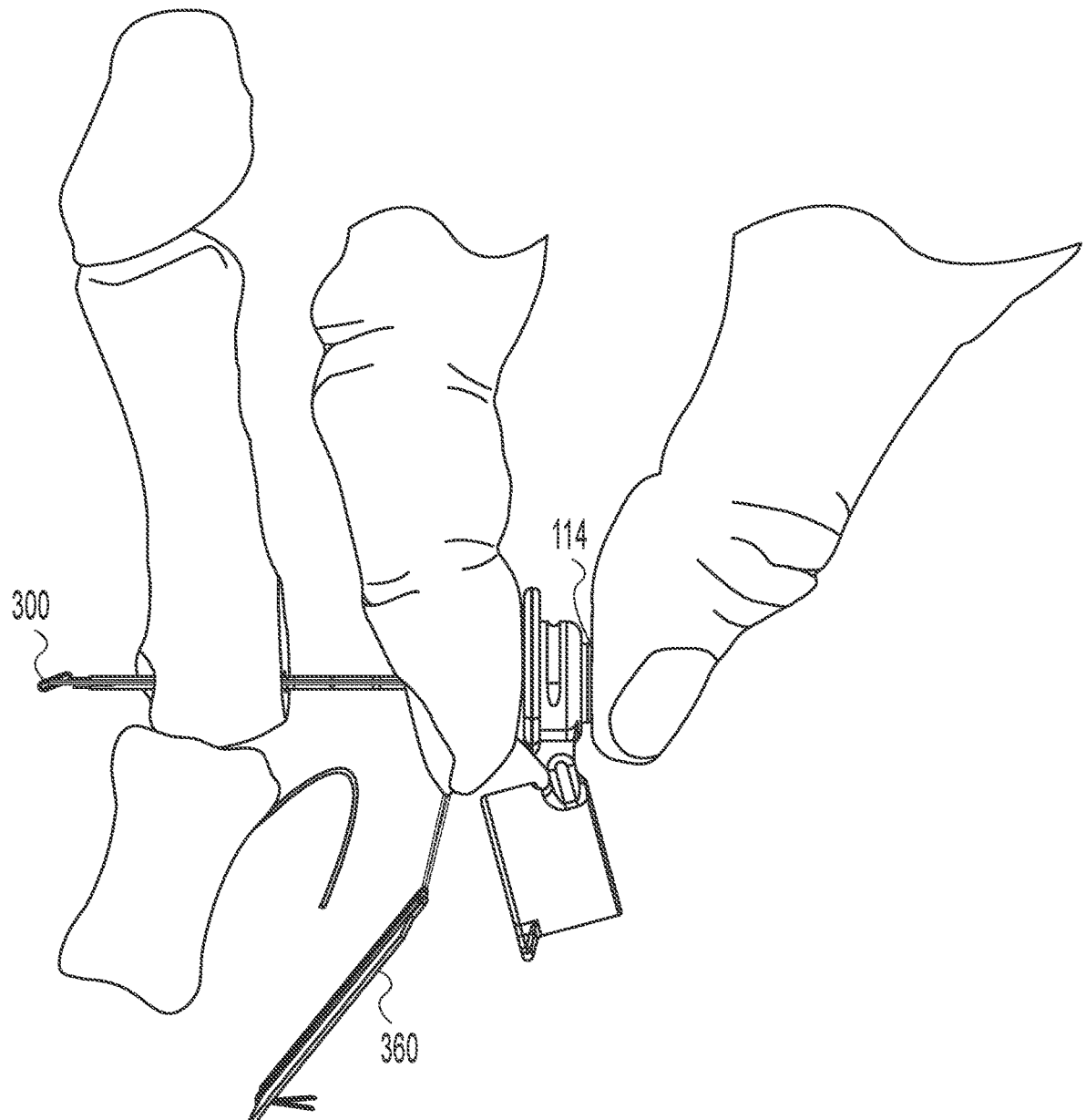

In FIG. 20, the suture reservoir 360 has been dislodged from the cap 130 and allowed to hang below the rest of the assembly 100. The button 114 has been pressed and the suture anchor 300 has been ejected from the end of the delivery tube causing it to begin to rotate.

Figure 21:
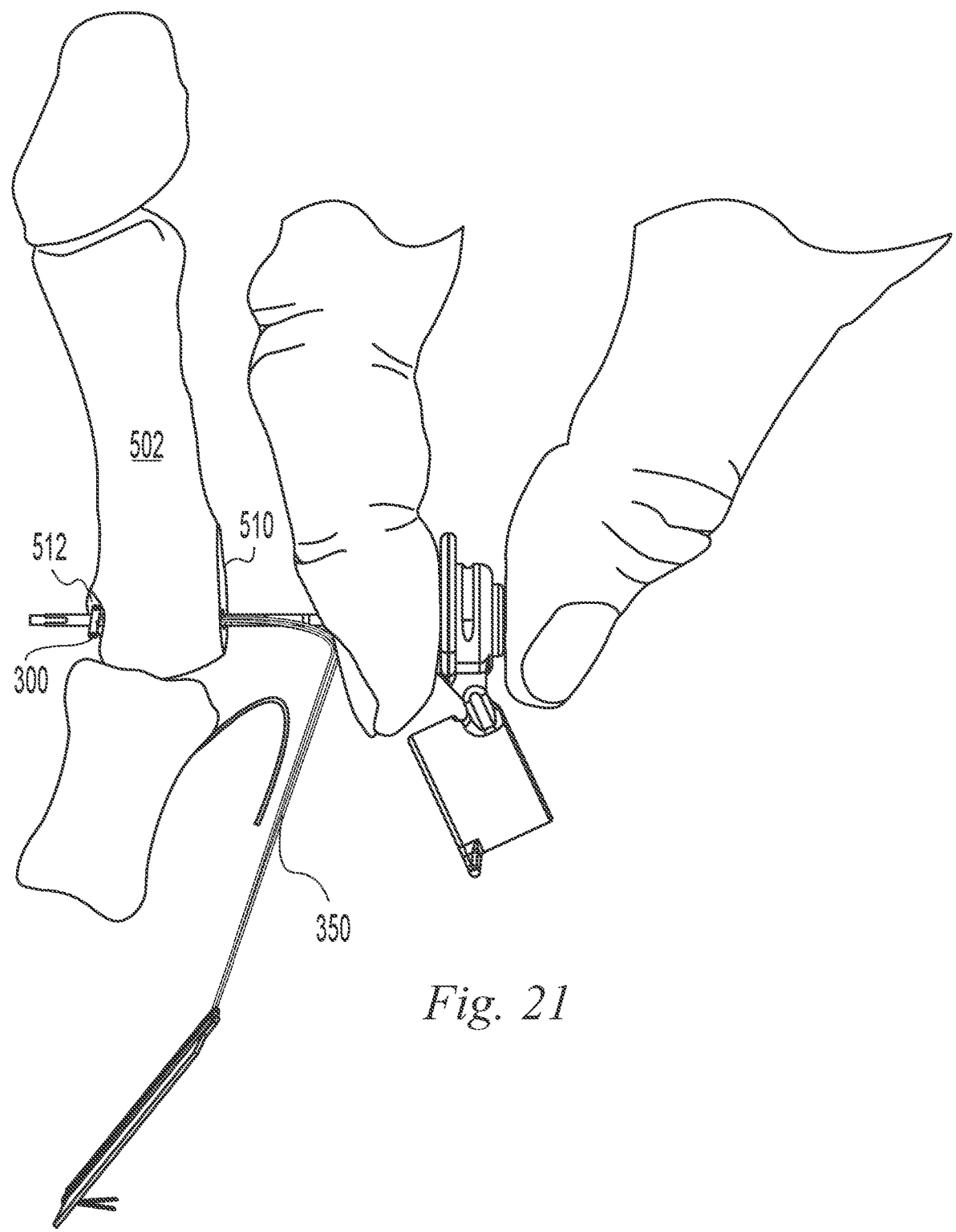

In FIG. 21, the suture 350 has been unwound from the trunnion and tensioned to further rotate the anchor 300 and position it against the cortical bone 512 opposite the decorticated region 510. In the illustrative example of FIG. 21, the suture 350 is optionally tensioned with the delivery tube still extending through the metatarsal bone 502. The delivery tube blocks the hole through the bone and thus ensures that the anchor will rotate and be positioned against the cortical bone in the deployed position rather than be pulled back through the hole.

Figure 22:
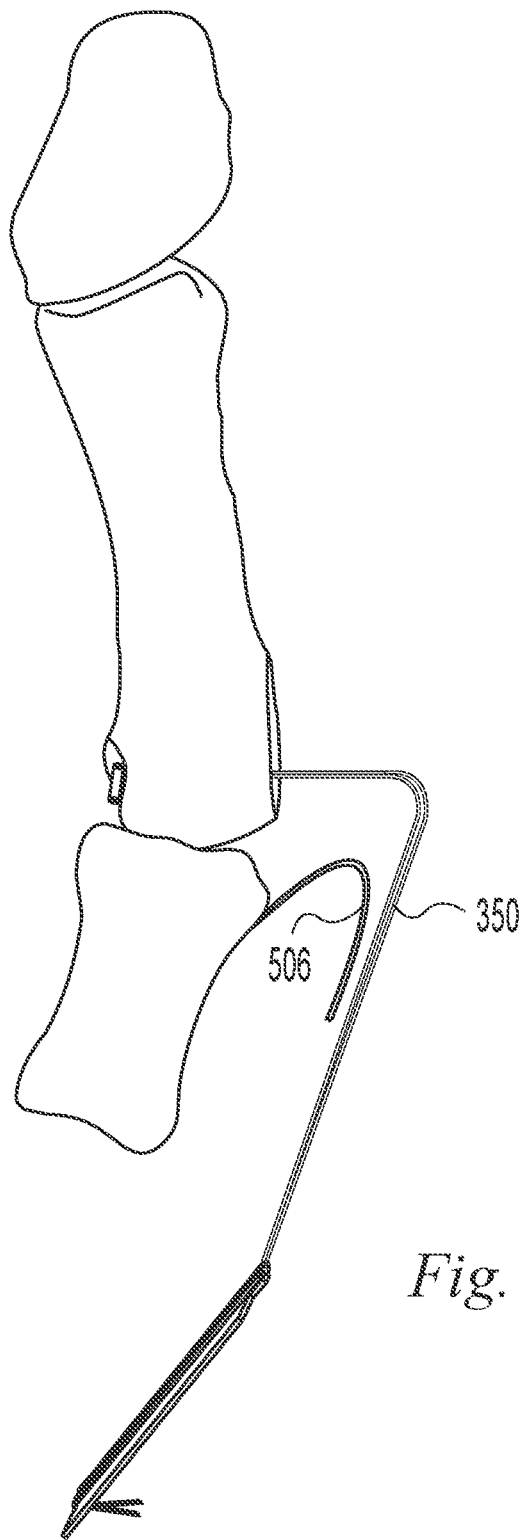

In FIG. 22, the delivery tube has been removed. Any number of anchors may be positioned by repeating the steps illustrated in FIGS. 17-22. The suture may be unwound from the suture reservoir 360 and used to repair the soft tissue 506.

FIGS. 23 and 24 illustrate dorsal and medial views of the medial capsular soft tissue 506 reattached over the decorticated region by passing the ends of the suture 350 through the soft tissue and tying them in a knot. The suture 350 may be passed through the soft tissue with a suture passer, manually with a needle attached to the ends of the suture 350, or by other suitable means known in the art.

Various examples have been illustrated and described. The various examples may be substituted and combined and other alterations made within the scope of the invention. For example, among other substitutions, male and female features may be reversed. The suture anchors may include features, such as additional holes, for coupling any number of sutures to the suture anchor. Needles may be supplied pre-attached to the suture ends and such needles may be attached to the suture reservoir 360. The following are additional illustrative examples according to the invention.

1. A suture anchor assembly comprising:
   a base member having a proximal end and a distal end;
   a delivery tube extending from the distal end of the base member, the delivery tube having a proximal end, a distal end, a longitudinal axis extending between the proximal end and the distal end, and a longitudinal passage;
   an ejector having a proximal end and a distal end, the ejector being positioned within the delivery tube for axial translation between a first position in which the distal end of the ejector is proximal to the distal end of the delivery tube and a second position in which the distal end of the ejector is distal to the first position, the ejector being moveable by a user to the second position;
   a safety device operable to prevent or allow movement of the ejector by a user to the second position; and
   a flip-type suture anchor positioned in the delivery tube distal to the distal end of the ejector.

2. The assembly of example 1 wherein the safety device is manually moveable by a user from a safe position in which it prevents the user from moving the ejector to a delivery position in which it allows the user to move the ejector to the second position.

3. The assembly of example 2 further comprising an actuator coupled to the proximal end of the ejector, the actuator extending from the proximal end of the base member, the safety device comprising a cap covering the actuator in the safe position.

4. The assembly of example 3 wherein the cap is hinged to the base member.

5. The assembly of example 3 wherein the ejector is resiliently biased by a first force to the first position, the actuator being responsive to a user applied force greater than the first force to move the ejector from the first position to the second position.

6. The assembly of example 3 wherein the base member includes a radial projection engageable by one or more of a user's fingers positioned distal to the radial projection and the actuator comprises a button engageable by a user's thumb positioned proximal to the button.

7. The assembly of example 1 further including a slot in a sidewall of the delivery tube adjacent the distal end of the delivery tube, the slot communicating through the sidewall to the longitudinal passage and being open at the distal end, the assembly further comprising a suture extending from the base member distally outside of the delivery tube, through the slot, and into engagement with the suture anchor.

8. The assembly of example 7 being responsive to movement of the ejector into the second position to press the suture anchor distally, wherein tension from the suture causes the suture anchor to rotate.

9. The assembly of example 7 wherein the base member further comprises a trunnion about which a portion of the suture is wound.
10. The assembly of example 9 further comprising a suture reservoir removably attached to the assembly, the reservoir containing a portion of the suture.
11. The assembly of example 10 wherein the reservoir comprises a body with a portion of the suture wound around the member.
12. The assembly of example 11 wherein the body comprises a flat card-like member having a tab and the safety device comprise a cap, the tab being removably retained by the cap.
13. The assembly of example 1 further comprising a hole forming instrument having an elongate shaft extending between a proximal end and a distal end, the elongate shaft having one or more reference marks indicating a plurality of length increments, the delivery tube having corresponding reference marks indicating the plurality of length increments.
14. The assembly of example 13 wherein the reference marks of the delivery tube are offset proximally from the distal end of the delivery tube.
15. A method of anchoring tissue to a bone, the method comprising:
    forming a hole in a bone from a first outer bone surface through the bone to a second outer bone surface with a hole forming instrument having an elongate shaft with a plurality of reference marks indicating a plurality of length increments;
    noting the position of the reference marks adjacent the first outer surface while a distal end of the elongate shaft is extending to or past the second outer surface;
    removing the hole forming instrument;
    inserting a delivery tube into the hole, the delivery tube having a plurality of reference marks corresponding to the reference marks on the hole forming instrument;
    indexing the delivery tube within the hole so that the tube is inserted relative to the first outer surface with the tube reference marks in the same position as noted relative to the hole forming instrument;
    ejecting a suture anchor from the delivery tube;
    tensioning a suture extending from the suture anchor to set the suture anchor against the second outer surface; and
    using the suture to secure the soft tissue adjacent the first outer surface.
16. The method of example 15 wherein the delivery tube reference marks are offset proximally from the distal end of the delivery tube.
17. A method of anchoring tissue to a bone, the method comprising:
    forming a hole in a bone from a first outer surface;
    removing the hole forming instrument;
    inserting a delivery tube into the hole;
    deactivating a safety device to enable ejection of a suture anchor from the delivery tube;
    ejecting a suture anchor from the delivery tube; and
    using a suture extending from the suture anchor to secure the soft tissue adjacent the first outer surface.
18. The method of example 17 wherein deactivating the safety device comprises moving a cap to expose an actuator.
19. The method of example 18 wherein moving the cap comprises rotating the cap about a hinge and further wherein the actuator comprises a spring biased pushbutton connected to an ejector.
20. The method of example 17 wherein the delivery tube is mounted to a base member, the base member including a radial projection engageable by one or more of a user's fingers positioned distal to the radial projection and an actuator comprising a button engageable by a user's thumb positioned proximal to the button, wherein ejecting a suture anchor comprises pressing the button.
21. The method of example 18 wherein moving the cap frees a suture reservoir mounted relative to the delivery tube, the method further comprising removing the suture reservoir and dispensing suture from the suture reservoir.
22. A method of anchoring tissue to a bone adjacent a metatarsophalangeal joint of a human foot, the method comprising:
    forming a hole in a portion of a bone adjacent a metatarsophalangeal joint from a first outer surface of the bone to a second outer surface of the bone;
    inserting a suture anchor through the hole;
    rotating the suture anchor to engage the second outer surface of the bone to prevent the suture anchor from passing back through the hole; and
    using a suture extending from the suture anchor to secure soft tissue adjacent the first outer surface.
23. The method of example 22 wherein the portion is a distal portion of a first metatarsal bone of a first ray of a human foot.
24. The method of example 23 further comprising performing a bunionectomy to remove a portion of the metatarsal bone creating a decorticated region on a medial side of the metatarsal bone.
25. The method of example 24 wherein forming a hole comprises forming a hole from the decorticated region through an opposite cortical surface.
26. The method of example 25 wherein using a suture extending from the suture anchor to secure soft tissue comprises securing capsular tissue of the metatarsophalangeal joint to the metatarsal bone.
27. The method of example 25 wherein inserting a suture anchor comprises:
    inserting a delivery tube into the hole;
    deactivating a safety device to enable ejection of the suture anchor from the delivery tube; and
    ejecting a suture anchor from the delivery tube.
28. The method of example 27 wherein the delivery tube is mounted to a base member, the base member including a radial projection engageable by one or more of a user's fingers positioned distal to the radial projection and an actuator comprising a button engageable by a user's thumb positioned proximal to the button, wherein ejecting a suture anchor comprises pressing the button.
29. The method of example 27 wherein deactivating the safety device comprises moving a cap to expose an actuator.
30. The method of example 29 wherein moving the cap comprises rotating the cap about a hinge and further wherein the actuator comprises a spring biased pushbutton connected to an ejector.
31. The method of example 29 wherein moving the cap frees a suture reservoir mounted relative to the delivery tube, the method further comprising removing the suture reservoir and dispensing suture from the suture reservoir.

What is claimed is:
1. A suture anchor assembly comprising:
    a base member having a proximal end and a distal end, the base member comprising a distally-facing surface;
    a delivery tube extending from the distal end of the base member, the delivery tube having a proximal end, a distal end, and a longitudinal passage;
    a suture anchor positioned in the delivery tube, the suture anchor defining a body that has a first side and a second side opposite the first side, and the suture anchor further comprising first and second through holes that extend through the body from the first side to the second side and are disposed on opposite sides of a midline of the body that is equidistantly disposed between first and second ends of the suture anchor that each extend from the first side to the second side; and a button actuatable distally toward the base member via pressure from a thumb of a hand, with one or more fingers of the hand pressing proximally against the distally-facing surface, to urge the suture anchor to move distally relative to the delivery tube, wherein the suture anchor is responsive to tension in a portion of a suture that extends from the base member through the first hole, which causes the suture anchor to pivot to a deployed orientation nonparallel to the delivery tube.

2. The suture anchor assembly of claim 1, wherein the distally-facing surface is proximate the distal end of the base member.

3. The suture anchor assembly of claim 1, wherein the distally-facing surface is part of a flange extending outward from the base member between the proximal end of the base member and the distal end of the base member.

4. The suture anchor assembly of claim 1, wherein, along a proximal-distal axis of the suture anchor assembly, the delivery tube is longer than the base member.

5. The suture anchor assembly of claim 1, wherein, prior to actuation, the button is displaced proximally from the distally-facing surface by a length that is less than a maximum width of the base member.

6. The suture anchor assembly of claim 1, wherein the portion of the suture is a first portion, and the suture anchor further comprising the suture arranged such that the first portion extends into the first hole and a second portion of the suture extends out the second hole.

7. The suture anchor assembly of claim 6, further comprising a suture reservoir removably attached to a remainder of the suture anchor assembly, the suture reservoir containing a portion of the suture.

8. The suture anchor assembly of claim 6, wherein:
the delivery tube comprises a sidewall that defines a slot, in communication with the longitudinal passage, that is open at the distal end of the delivery tube; and
the suture extends from the base member distally outside of the delivery tube, through the slot, and into engagement with the suture anchor.

9. The suture anchor assembly of claim 1, further comprising a safety device comprising:
a safe position in which the safety device prevents user actuation of the button; and
a delivery position, in which the safety device permits user actuation of the button.

10. The suture anchor assembly of claim 1, further comprising a hole forming instrument having an elongate shaft extending between a proximal end and a distal end, the elongate shaft having one or more reference marks indicating a plurality of length increments;
wherein the delivery tube comprises corresponding reference marks indicating the plurality of length increments.

11. The suture anchor assembly of claim 1, further comprising:
a suture connected to the suture anchor such that, in response to motion of the suture distally out of the delivery tube, tension on the suture urges the suture anchor to rotate to an orientation nonparallel to the delivery tube; and
a safety device comprising:
a safe position in which the safety device prevents user actuation of the button; and
a delivery position, in which the safety device permits user actuation of the button.

12. A suture anchor assembly comprising:
a base member having a proximal end and a distal end, the base member further including a trunnion configured to attach to a suture;
a delivery tube extending from the distal end of the base member, the delivery tube having a proximal end, a distal end, and a longitudinal passage;
a suture anchor positioned in the delivery tube;
a suture reservoir attached to a remainder of the suture anchor assembly, the suture reservoir configured to attach to an additional portion of the suture: and
a button actuatable into the base member via pressure from a thumb of a hand to urge the suture anchor to move distally relative to the delivery tube;
wherein the base member comprises a radial projection positioned distal of the button such that the button is actuatable into the base member by pressing the button with a thumb of a hand while holding the base member with one or more fingers of the hand on the radial projection.

13. The suture anchor assembly of claim 12, wherein the radial projection is part of a flange extending outward from the base member between the proximal end of the base member and the distal end of the base member.

14. The suture anchor assembly of claim 12, wherein, along a proximal-distal axis of the suture anchor assembly, the delivery tube is longer than the base member.

15. The suture anchor assembly of claim 12, wherein, prior to actuation, the button is displaced proximally from the radial projection by a length that is less than a maximum width of the base member.

16. The suture anchor assembly of claim 12, wherein the radial projection is disposed distal of the trunnion.

* * * * *